(12) United States Patent
Wang et al.

(10) Patent No.: US 10,647,745 B2
(45) Date of Patent: May 12, 2020

(54) COMPOUND FOR TREATING SEQUELAE OF ISCHEMIC CEREBRAL STROKE

(71) Applicant: Jingyi Wang, Suzhou, Jiangsu (CN)

(72) Inventors: Jingyi Wang, Suzhou (CN); Jianling Zuo, Suzhou (CN); Xiaoliang Lv, Suzhou (CN); Tan Zhang, Haikou (CN)

(73) Assignee: Jingyi Wang, Jiangsu (CN)

( * ) Notice: Subject to any disclaimer, the term of this patent is extended or adjusted under 35 U.S.C. 154(b) by 0 days.

(21) Appl. No.: 16/059,174

(22) Filed: Aug. 9, 2018

(65) Prior Publication Data

US 2019/0040101 A1    Feb. 7, 2019

Related U.S. Application Data

(62) Division of application No. 15/236,055, filed on Aug. 12, 2016, now abandoned.

(30) Foreign Application Priority Data

Aug. 14, 2015 (WO) ................. PCT/CN2015/087048

(51) Int. Cl.
*C07K 7/06* (2006.01)
*A61K 38/08* (2019.01)
*A61K 38/00* (2006.01)

(52) U.S. Cl.
CPC ............... *C07K 7/06* (2013.01); *A61K 38/08* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2011/0045008 A1* | 2/2011 | Karpatkin | C07K 7/06 424/179.1 |
| 2011/0150764 A1 | 6/2011 | Lee et al. | |
| 2012/0252071 A1 | 10/2012 | Greif et al. | |

FOREIGN PATENT DOCUMENTS

EP    2338899 A1    6/2011

OTHER PUBLICATIONS

Yampolsky, Lev Y. and Stolzfus, Arlin; "The exchangeability of amino acids in proteins." Genetics (2005) 170 p. 1459-1472.*
Schaur E et al.: "Neuroprotection of Cerebrolysin in tissue culture models of brain ischemia: post lesion application Indicates a wide therapeutic window", Journal of Neural Transmission, vol. 113, No. 7, Dec. 14, 2005 (Dec. 14, 2005), pp. 855-868.
Wu et al.: "Neuroprotection in Experimental Stroke with Targeted Neurotrophins", Journal of the American Society for Experimental Neurotherapeutics, vol. 2, No. 1, Jan. 1, 2005 (Jan. 1, 2005), pp. 120-128.
Wang et al.: "Enhanced anti-ischemic stroke of ZL006 by T7-conjugated PEGylated lipsomes drug delivery system", Scientific Reports, vol. 5: 12651, Jul. 29, 2015 (Jul. 29, 2015), 15 pages.
Hirst, Margaret et al, "Human gmp synthetase." J. Biol. Chem. (1994) 269(38) pp. 23830-23837.
Myriad-Mayo guidance of Mar. 2014.
Hu, Aizong and Norrby, Erling; "Role of individual cysteine residues in the processing and antigenicity of the measles virus haemagglutinin protein." J. Gen. Virol. (1994) 75 pp. 2173-2181.

* cited by examiner

*Primary Examiner* — Fred H Reynolds
(74) *Attorney, Agent, or Firm* — Womble Bond Dickinson (US) LLP; Cristin H. Cowles; Sai Seetharaman

(57) ABSTRACT

The present invention provides a compound (I) for treating sequelae of ischemic cerebral stroke:

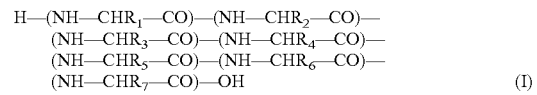

or a pharmaceutically acceptable salt thereof, wherein $R_1$-$R_7$ are defined herein. The present invention also provides a pharmaceutical composition comprising said compound and use of the same in the manufacture of a medicament for treating sequelae of ischemic cerebral stroke. The compound and pharmaceutical composition according to the present invention have good pharmacological activities so that they are able to improve significantly the symptom of sequelae of ischemic cerebral stroke.

2 Claims, 10 Drawing Sheets
Specification includes a Sequence Listing.

SEQUENCE LISTING

<160> NUMBER OF SEQ ID NOS: 2

<210> SEQ ID NO 1

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Val His Ser Val Gln Leu Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (2)..(2)
<223> OTHER INFORMATION: His(Trt)
<220> FEATURE:
<221> NAME/KEY: VARIANT
<222> LOCATION: (3)..(3)
<223> OTHER INFORMATION: Ser(tBu)
<220> FEATURE:
<221> NAME/KEY: VARIANT
<222> LOCATION: (5)..(5)
<223> OTHER INFORMATION: Gln(Trt)
<220> FEATURE:
<221> NAME/KEY: VARIANT
<222> LOCATION: (7)..(7)
<223> OTHER INFORMATION: Tyr(tBu)

<400> SEQUENCE: 2

Val Xaa Xaa Val Xaa Leu Xaa
1               5
```

COMPOUND FOR TREATING SEQUELAE OF ISCHEMIC CEREBRAL STROKE

RELATED APPLICATIONS

This application is a divisional of U.S. Non-Provisional patent application Ser. No. 15/236,055, filed Aug. 12, 2016, which claims the benefit of priority to-International Patent Application No. PCT/CN2015/087048, filed Aug. 14, 2015, which are incorporated by reference herein in their entirety.

SEQUENCE LISTING

The instant application contains a Sequence Listing which has been submitted in ASCII format via EFS-Web and is hereby incorporated by reference in its entirety. Said ASCII copy, created on Aug. 8, 2018, is named 2018-08-08_W103046_1010 USD1_SequenceListing.txt and is 917 bytes in size.

TECHNICAL FIELD

The present invention relates to a medicinal compound for treating sequelae of ischemic cerebral stroke and the use of the same in the manufacture of a medicament for treating sequelae of ischemic cerebral stroke.

BACKGROUND ART

Cerebral stroke is a disease in which a cerebral tissue damage is caused by a sudden blood vessle rupture or by a blood circulation disturbance arising from vascular obstruction in brain. Ischemic cerebral stroke means necrosis of local cerebral tissues including neurocytes, neurogliocytes, and blood vessel due to deficient in blood supply. The fundamental cause of the ischemic cerebral stroke is that the extracranial or intracranial arteries leading to the brain have occlusive lesions and fail to achieve prompt and adequate collateral circulation so that the metabolism requirement of the local cerebral tissues cannot be met by the available blood supply. The incidence of ischemic cerebral stroke is higher than that of hemorrhagic cerebral stroke and accounts for 60%-70% of all cerebral stroke cases. The occlusion and stenosis in internal carotid and vertebral arteries may cause ischemic cerebral stroke in people older than 40 in a higher frequency in males than in females. Some severe cases result in death.

The sequelae of ischemic cerebral stroke means the symptoms of hemiplegia, speech disorder, or facial paralysis and the like occurred after the ischemic cerebral stroke, collectively referred to as sequelae of ischemic cerebral stroke. Mainly, these include the following symptoms: semiplegia (hemiplegia), hemi-limb disabilities, numbness of limbs, hemianopsia, aphasia, or crossed hemiplegia, contralateral sensory disturbance, e external ophthalmoplegia, nystagmus, dyslalia, speech disorder, memory deterioration, facial paralysis, dysphagia, choking on food and drink, dystaxia, dizzy and headache, and the like.

Reckoning on the survey data obtained 20 years ago, there are about 2 million of new cerebral stroke cases every year in China, more than 150 million persons died from cerebral stroke every year, and there are about 600-700 million survived from cerebral stroke. Among the survival patients, about 75%-80% would have different levels of sequelae, with over 40% of severe disability. About ¼ to ⅓ of them may relapse within 2 to 5 years. With the improvement in living standards and the change of the life style in recent years, the population incidence of cerebral stroke is still rising in China. In particular, because of the improvement of medical conditions and the advancement of clinical technology, the mortality rate of stroke significantly declined while, however, leading to a great increase in the morbidity of the sequelae of cerebral stroke, which causes a greater disease burden. The cerebral stroke has become a leading disease that jeopardizes the health of middle aged and elderly people in China.

At present, butylphthalide (NBP) is a drug approved for the treatment of sequelae of ischemic cerebral stroke. The sodium chloride injection of butylphthalide (which has the principal component of butylphthalide with a chemical name of dl-3-n-butylphthalide (called as butylphthalide or NBP for short)) is used for improving neurological function deficits in a patient with acute ischemic cerebral stroke. The drug is administered through an intravenous drip within 48 hours from the onset of the disease, twice per day, each 25 mg (100 ml) over a period of less than 50 minutes with a time interval of not less than 6 hours between two administrations during a treatment course of 14 days. Since a PVC infusion device has a significant absorption effect on butylphthalide, a PE infusion device can only be used for the infusion of the butylphthalide product. There is no research data about the efficacy or safety of the drug administered 48 hours after the onset of the disease. The butylphthalide soft capsule has an indication of mild or moderate acute ischemic cerebral stroke. In a specification of 0.1 g, the drug is administered orally under fasting, two capsules (0.2 g) every time, four times every day during a treatment course of 10-12 days, or as recommended by the doctor. Unwanted effects include mild transaminase elevation, which can be normalized after drug withdrawal according to some follow-up cases. Nausea, abdominal discomfort, rash, psychiatric symptoms and the like happen occasionally.

In addition, aspirin is also used to treat sequelae of ischemic cerebral stroke. Aspirin has a generic name of acetylsalicylic acid, and is an antipyretic analgesics with a long history since its discovery in 1899. It has been used for treating cold, fever, headache, toothache, arthralgia, and rheumatism, and is capable of inhibiting platelet aggregation, thereby preventing and treating ischemic cardiopathy, angina, cardiopulmonary infarction, and cerebral thrombosis. However, aspirin has no significant efficacy on the treatment of sequelae of ischemic cerebral stoke, but has multiple adverse effects. Accordingly, when aspirin is used to treat various diseases, one should keep close watch over its adverse effects.

Therefore, there still is a great need now to develop a new medicinal substance for treating sequelae of ischemic cerebral stroke in the current society.

SUMMARY OF THE INVENTION

It is one objective of the present invention to provide a compound represented by the following formula (I) or the pharmaceutically acceptable salt thereof for treating sequelae of ischemic cerebral stroke:

$$H-(NH-CHR_1-CO)-(NH-CHR_2-CO)-(NH-CHR_3-CO)-(NH-CHR_4-CO)-(NH-CHR_5-CO)-(NH-CHR_6-CO)-(NH-CHR_7-CO)-OH \quad (I)$$

wherein each of $R_1$-$R_7$ is independently selected from the group consisting of alkyl, alkenyl, alkynyl, alkoxyl, or alkylthio which are optionally substituted by one or more substituents selected from the group consisting of halo, hydroxyl, sulfydryl, carboxyl, amino, nitro, cyano, carbamoyl, optionally substituted cycloalkyl, optionally substituted aryl, and optionally substituted heteroaryl, wherein the substituents in the optionally substituted cycloalkyl, optionally substituted aryl and optionally substituted heteroaryl are one or more selected from the group consisting of hydroxyl, sulfydryl, amino, nitro, cyano, and carboxyl.

Preferably, the present invention provides a compound of formula (I):

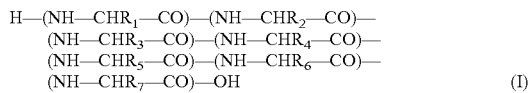

$$\text{H—(NH—CHR}_1\text{—CO)—(NH—CHR}_2\text{—CO)—} \\ \text{(NH—CHR}_3\text{—CO)—(NH—CHR}_4\text{—CO)—} \\ \text{(NH—CHR}_5\text{—CO)—(NH—CHR}_6\text{—CO)—} \\ \text{(NH—CHR}_7\text{—CO)—OH} \quad (I)$$

wherein each of $R_1$, $R_4$ and $R_6$ is independently selected from the group consisting of $C_1$-$C_6$ alkyl, $C_2$-$C_6$ alkenyl, or $C_2$-$C_6$ alkenyl;

$R_2$ is $C_1$-$C_6$ alkyl which is substituted with five to ten membered heteroaryl optionally substituted with halo, hydroxyl, sulfydryl, carboxyl, amino, nitro, or cyano;

$R_3$ is $C_1$-$C_6$ alkyl group substituted by halo, hydroxyl, sulfydryl, or amino;

$R_5$ is $C_1$-$C_6$ alkyl substituted with carbamoyl; and $R_7$ is $C_1$-$C_6$ alkyl which is substituted with C6-C14 aryl optionally substituted with halo, hydroxyl, sulfydryl, carboxyl, amino, nitro, or cyano;

or a pharmaceutically acceptable salt thereof.

In one aspect, the present invention provides a method for preparing a compound of formula (I), which links multiple monomeric units together through a condensation reaction using a conventional polymerization method in the art, in particular a solid phase synthesis method and results in the desired compound.

In one aspect, the present invention provides a pharmaceutical composition comprising the compound of formula (I). The pharmaceutical composition comprises at least one compound according to the invention and optionally a pharmaceutically acceptable carrier.

In one aspect, the present invention also provides the use of the compound according to the invention or a pharmaceutical composition comprising the same in the manufacture of a medicament for treating sequelae of ischemic cerebral stroke.

DETAILED DESCRIPTION

Definitions

Figure 1:
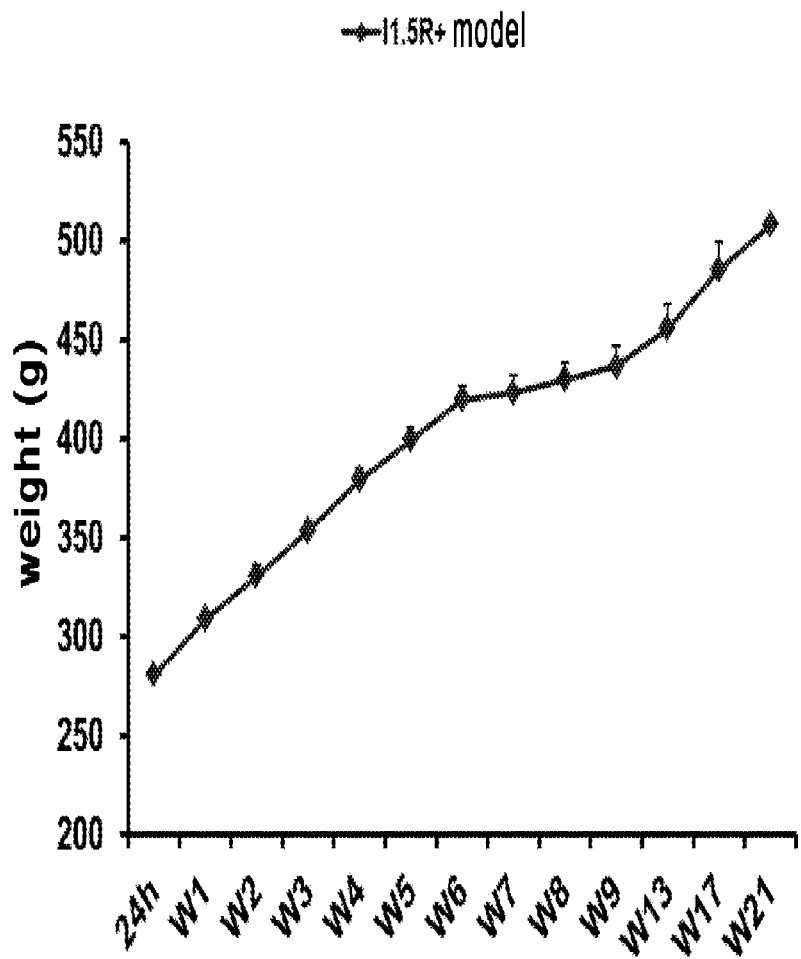
FIG. 1 illustrates the weight conditions of rats at different times (observed until 22 weeks) in a rat 1.5 h ischemia-reperfusion model.

As used herein, the term "alkyl" refers to a straight or branched chain alkane hydrocarbon group containing a specified number of carbon atoms, such as $C_1$-$C_{18}$ alkyl, $C_1$-$C_{12}$ alkyl, $C_1$-$C_6$ alkyl, $C_1$-$C_4$ alkyl and the like. Examples of alkyl include, but are not limited to, methyl, ethyl, n-propyl, iso-propyl, n-butyl, iso-butyl, tert-butyl, pentyl, iso-pentyl, neo-pentyl, hexyl, heptyl, octyl, nonyl, decyl and the like.

The term "alkenyl" refers to a straight or branched chain alkene hydrocarbon group containing a specified number of carbon atoms, such as $C_2$-$C_{12}$ alkenyl, $C_2$-$C_6$ alkenyl, $C_2$-$C_4$ alkenyl and the like. Examples of alkenyl include, but are not limited to, vinyl, propenyl, butenyl, pentenyl, hexenyl, heptenyl, octenyl, nonenyl, decenyl and the like.

The term "alkynyl" refers to a straight or branched alkyne hydrocarbon group containing a specified number of carbon atoms, such as $C_2$-$C_{12}$ alkynyl, $C_2$-$C_6$ alkynyl, $C_2$-$C_4$ alkynyl and the like. Examples of alkynyl include, but are not limited to, ethynyl, propynyl, butynyl, pentynyl, hexynyl, heptynyl, octynyl, nonenyl, decynyl, and the like.

The term "cycloalkyl" refers to a hydrocarbon group of saturated 3-8 membered monocyclic system. Specific examples of cycloalkyl include, but are not limited to, cyclopropyl, cyclobutyl, cyclopentyl, cyclohexyl, cycloheptyl, cyclooctyl and the like.

The term "aryl" refers to a monocyclic aromatic group or a condensed or non-condensed polycyclic aromatic group containing 6-14 carbon atoms, preferably 6-10 carbon atoms. Examples of aryl preferably are, but are not limited to, phenyl, bi-phenyl, naphthyl, anthryl, 5,6,7,8-tetrahydronaphthyl, 2,3-dihydrobenzofuryl, and the like.

The term "heteroaryl" refers to a five to ten membered aromatic cyclic group containing 1-4 heteroatoms selected from nitrogen, sulfur or oxygen as ring atoms. The heteroaryl may be a monocyclic heteroaryl group containing 5-6 ring atoms, or a bicyclic heteroaryl group containing 7-10 ring atoms. Examples of the heteroaryl include, but are not limited to, pyrrolyl, pyrazolyl, imidazolyl, oxazolyl, thienyl, iso-oxazolyl, oxadiazolyl, thiazolyl, triazolyl, tetrazolyl, pyridinyl, pyrimidinyl, furyl, indolyl, quinolyl, iso-quinolyl, benzofuryl, benzothienyl, benzimidazolyl, benzopyrazolyl, benzoxazolyl, benzoisooxazolyl, benzothiazolyl and the like.

The term "halo" refers to —F, —Cl, —Br, or —I.

The term "alkoxyl" refers to —O-alkyl.

The term "alkylthio" refers to —S-alkyl.

The term "pharmaceutically acceptable salt" includes, but is not limited to, organic acid salts, inorganic acid salts, metal salts, ammonium salts and inner salts of the compounds according to the present invention, among which the organic acid salts include, but are not limited to, tosilate, mesylate, malate, acetate, citrate, lactate, ascorbate, tartrate, succinate, fumarate, maleate, oxalate, malonate, and the like; the inorganic acid salts include, but are not limited to, hydrochloride, sulphate, phosphate, nitrate, hydrobromide, hydroiodate, sulfite, carbonate, bicarbonate, bisulphate, dihydrophosphate, hydrophosphate, and the like; and the metal salts include, but are not limited to, sodium salts, potassium salts, lithium salts, magnesium salts, calcium salts, ferric salts, and the like.

The term "pharmaceutically acceptable carrier" includes conventional excipients, diluents, disintegrants, binders, lubricants, sweeteners, stabilizers, solubilizers preservatives, and the like.

The term "prevention" refers to completely or partly preventing the occurrence of a disease or the symptoms thereof.

The term "treat" refers to completely or partly alleviating or curing a disease or the symptoms thereof, comprising (a) alleviating the symptoms of the disease and (b) eliminating, the symptoms of the disease.

Preferably, in the compound of formula (I) or a pharmaceutically acceptable salt provided herein, each of $R_1$-$R_7$ is independently selected from the group consisting of optionally substituted $C_1$-$C_{18}$ alkyl (preferably $C_1$-$C_{12}$ alkyl, more preferably $C_1$-$C_6$ alkyl, more preferably methyl, ethyl, propyl, iso-propyl, n-butyl, iso-butyl, tert-butyl, pentyl, hexyl), optionally substituted $C_2$-$C_{12}$ alkenyl (preferably $C_2$-$C_6$ alkenyl, more preferably $C_2$-$C_4$ alkenyl, more preferably vinyl, propenyl, butenyl), optionally substituted $C_2$-$C_{12}$ alkynyl (preferably $C_2$-$C_6$ alkynyl, more preferably $C_2$-$C_4$ alkynyl, more preferably ethynyl, propynyl, butynyl), optionally substituted $C_1$-$C_{18}$ alkoxyl (preferably $C_1$-$C_{12}$ alkoxyl, more preferably $C_1$-$C_6$ alkoxyl, more preferably methoxyl, ethoxyl, propoxyl, butoxyl, pentyloxyl, hexyloxyl), and optionally substituted $C_1$-$C_{18}$ alkylthio (preferably $C_1$-$C_{12}$ alkylthio, more preferably $C_1$-$C_6$ alkylthio, more preferably methylthio, ethylthio, propylthio, butylthio, pentylthio, hexylthio), wherein the substituents are one or more selected from the group consisting of halo, hydroxyl, sulfydryl, carboxyl, amino, nitro, cyano, carbamoyl, optionally substituted $C_3$-$C_8$ cycloalkyl, optionally substituted $C_6$-$C_{14}$ aryl and optionally substituted five to ten membered heteroaryl; and in the optionally substituted $C_3$-$C_8$ cycloalkyl, optionally substituted $C_6$-$C_{14}$ aryl and optionally substituted $C_6$-$C_{10}$ heteroaryl, the substituents are one or more selected from the group consisting of hydroxyl, sulfydryl, amino, nitro, cyano, and carboxyl.

Preferably, in the compound of formula (I) or a pharmaceutically acceptable salt thereof provided herein, each of $R_1$-$R_7$ is independently selected from the group consisting of optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxyl, and optionally substituted $C_1$-$C_6$ alkylthio, wherein the substituents are one or more selected from the group consisting of halo, hydroxyl, sulfydryl, carboxyl, amino, nitro, cyano, and carbamoyl, optionally substituted $C_3$-$C_8$ cycloalkyl, optionally substituted $C_6$-$C_{14}$ aryl and optionally substituted five to ten membered heteroaryl, and in the optionally substituted $C_3$-$C_8$ cycloalkyl, optionally substituted $C_6$-$C_{14}$ aryl and optionally substituted five to ten membered heteroaryl, the substituents are one or more selected from the group consisting of hydroxyl, sulfythyl, amino, nitro, cyano, and carboxyl.

Preferably, in the compound of formula (I) or a pharmaceutically acceptable salt thereof provided herein, each of $R_1$-$R_7$ is independently selected from the group consisting of optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxyl, and optionally substituted $C_1$-$C_6$ alkylthoi; and wherein $R_2$ is optionally substituted with five to ten membered heteroaryl; $R_3$ is optionally substituted with halo, hydroxyl, sulfydryl, carboxyl, amino, nitro, or cyano; $R_5$ is optionally substituted with carboxyl, or carbamoyl; and $R_7$ is optionally substituted with $C_6$-$C_{14}$ aryl optionally substituted with halo, hydroxyl, sulfydryl, carboxyl, amino, nitro, or cyano.

Preferably, in the compound of formula (I) or a pharmaceutically acceptable salt thereof provided herein, the $C_6$-$C_{14}$ aryl is selected from the group consisting of phenyl, naphthyl, anthryl, and the like; the five to ten membered heteroaryl is selected from the group consisting of pyrrolyl, pyrazolyl, imidazolyl, oxazolyl, thienyl, iso-oxazolyl, oxadiazolyl, thiazolyl, triazolyl, tetrazolyl, pyridinyl, pyrimidinyl, furyl, indolyl, quinolyl, isoquinolyl, benzofuryl, benzothienyl, benzimidazolyl, benzopyrazolyl, benzoxazolyl, benzoisooxazolyl, benzothiazolyl and the like.

Preferably, in the compound of formula (I) or a pharmaceutically acceptable salt thereof provided herein, the heteroaryl is selected from five to six membered heteroaryl.

Preferably, in the compound of formula (I) or a pharmaceutically acceptable salt thereof provided herein, the heteroaryl is selected from the group consisting of pyrrolyl, pyrazolyl, imidazolyl, oxazolyl, thienyl, iso-oxazolyl, oxadiazolyl, thiazolyl, triazolyl, tetrazolyl, pyridinyl, pyrimidinyl, furyl, indolyl, quinolyl, isoquinolyl, benzofuryl, benzothienyl, benzimidazolyl, benzopyrazolyl, benzoxazolyl, benzoisooxazolyl, and benzothiazolyl.

Preferably, in the compound of formula (I) or a pharmaceutically acceptable salt thereof provided herein, the aryl is selected from the group consisting of phenyl, naphthyl, and anthryl.

Preferably, in the compound of formula (I) or a pharmaceutically acceptable salt thereof provided herein, the alkyl is selected from the group consisting of methyl, ethyl, propyl, iso-propyl, n-butyl, iso-butyl, tert-butyl, pentyl, iso-pentyl, neo-pentyl, and hexyl; the alkenyl is selected from the group consisting of vinyl, propenyl, butenyl, pentenyl, and hexenyl; the alkynyl is selected from the group consisting of ethynyl, propynyl, butynyl, pentynyl, and hexynyl.

In a preferable embodiment of the present invention, the compound according to the invention has the following structure:

(SEQ ID NO.: 1)

(III)

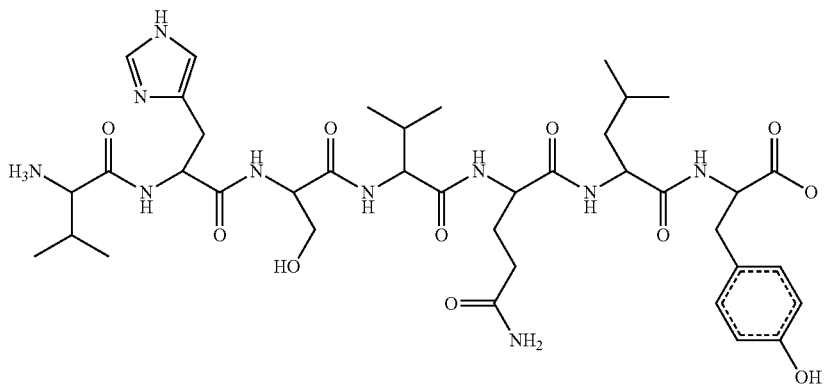

The compounds according to the present invention can be prepared by a conventional organic chemical synthesis method. Specifically, the compounds according to the present invention can be prepared by a solid phase synthesis method commonly used in the art, wherein a polymeric resin is used as an insoluble solid phase support. Firstly, a first amino acid protected at its N-terminal (e.g. with a protective group of Fmoc) is covalently linked to the solid phase support. Under a basic condition, the amino group is deprotected. Then a condensation reaction between the carboxyl of a second amino acid likely protected at its N-terminal and the amino of the first amino acid linked to the solid phase support is carried out to form a peptide bond. Through the similar steps, other amino acids are further linked to the amino terminal of the second amino acid until the desired peptide chain backbone is formed. Then, the peptide chain is separated from the resin under suitable reaction conditions and other protecting groups remained in the peptide chain are removed. And final products are obtained through purification.

The present invention also provides a pharmaceutical composition comprising the compound according to the present invention, which comprises the compound as described herein and optionally a pharmaceutically acceptable carrier. To prepare a pharmaceutical composition comprising the compound described herein, the pharmaceutically acceptable carrier may be solid or liquid. Among others, the solid carrier may be one or more materials used as excipients, diluents, sweeteners, solubilizers, lubricants, binders, tablet disintegrants, stabilizers, preservatives, or encapsulating materials. The liquid carrier may be solvents or liquid dispersion media. Suitable solid carriers include, but are not limited to, for example, cellulose, glucose, lactose, mannitol, magnesium stearate, magnesium carbonate, saccharin sodium, sucrose, dextrin, talc, starch, pectin, gelatin, tragacanth, arabic gum, sodium alginate, parabens, methylcellulose, sodium carboxymethyl cellulose, a low-melting point wax, cocoa butter, and the like. Suitable liquid carriers include, but are not limited to, water, ethanol, polylol (such as glycerol, propanediol, liquid polyethylene glycol, etc), a vegetable oil, glyceride and a mixture thereof.

The pharmaceutical composition according to the present invention may be prepared by a known method, including conventional blending, granulating, tableting, coating, dissolving, or lyophilization processes.

The pharmaceutical composition according to the present invention may be administered to the patients via various routes, such as oral, local (such as topical), systemic, intravenous, intramuscular, or mucosal.

Depending on the administration route, the pharmaceutical composition according to the present invention may be prepared into various dosage forms conventional in the art, such as tablet, capsule, pill, emulsion, injection, pelvis, granule, ointment, patch, powder injection, suspension, cream, aerosol, drop, lozenge, and the like.

In a tablet, an active ingredient can be blended with a carrier having required binding capacity in an appropriate ratio and pressed into a desired shape and size. In a powder dosage form, a carrier is finely divided solids blended with a finely divided active ingredient. A powder and tablet generally contains about 5 or 10% to about 70% of active ingredient. Suitable carriers include, for example, magnesium carbonate, magnesium stearate, talc, sugars, lactose, pectin, dextrin, starch, gelatin, tragacanth, methyl cellulose, sodium carboxymethylcellulose, low-melting-point wax, cocoa butter and the like.

The compound described herein can be formulated for parenteral administration (e.g. through injection) and may be present in a unit dosage form in an ampoul, a pre-filled syringe, a small-volume infusion bottle, or in a multiple dose container. The composition may be in the form of suspensions, solutions, or emulsions in an oily or aqueous medium. Alternatively, the active ingredients may be in the form of powders before use, which is obtained by sterile separation of sterile solids or lyophilization of solutions, and may be reconstituted in a suitable medium such as sterile and pyrogen-free water.

An aqueous solution suitable for oral use can be prepared by dissolving the active ingredient into water and adding suitable colorants, sweeteners, preservatives, stabilizers and/or solubilizers as needed.

An aqueous suspension suitable for oral use can be prepared by dispersing the finely divided active ingredient into water with viscous materials such as a natural or synthetic gum, resin, methylcellulose, sodium carboxylmethylcellulose, or other well-known suspending agents.

The compound described herein can be formulated into a form of ointment, cream, or transdermal patch for local administration to epidermis. The ointment or cream can be formulated with, for example, an aqueous or oily matrix added with a suitable thicker and/or gelling agent.

The administration to respiratory tract can be implemented using an aerosol formulation, wherein the active ingredient is provided in a pressurized package having suitable propellants (such as chlorofluorocarbon (e.g. dichlorodifluoromethane, trichlorofluoromethane or dichlorotetrafluoroethane), carbon dioxide or other suitable gases). The aerosol can conveniently comprise surfactants (such as lecithin). The drug dosage can be controlled by a metering valve.

In addition, if needed, a formulation suitable for sustained release, delayed release, or retarded release may also be used.

The pharmaceutical formulation is preferably in a unit dosage form, in which the formulation is subdivided into unit dosages containing a suitable amount of active ingredient. The unit dosage form can be packed in a package containing discrete quantities of the formulation, such as packaged tablets, capsules, or powders in vials or ampoules The present invention also provides use of the compound or pharmaceutical composition according to the present invention in the manufacture of a medicament, in particular a medicament for treating sequelae of ischemic cerebral stroke. Accordingly, the present invention provides a method for treating sequelae of ischemic cerebral stroke, comprising administering a therapeutically effective amount of the pharmaceutical composition comprising at least one compound according, to the present invention or a pharmaceutically acceptable salt thereof and a pharmaceutically acceptable carriers to a patient in need thereof. In another aspect, the present invention provides a method for treating sequelae of ischemic cerebral stroke, comprising administering a therapeutically effective amount of at least one compound according to the present invention or a pharmaceutically acceptable salt thereof to a patient in need thereof. In another aspect, the present application provides the compound of the present application for the use of treating sequelae of ischemic cerebral stroke. The precise dosage required is determined based on the attendant physician's judgment. Generally, the dosage of the active compound to be administered may be, for example, about 0.1 to about 100 mg per day, about 0.1 to about 75 mg/day, about 0.1 to about 50 mg/clay, or about 5 to about 10 mg/day. The desired dosage depends on the specific compound used, severity of disease, administration route, weight and healthy condition of the patient as well as the attendant physician's judgment.

EXAMPLES

The present invention will be illustrated in more details in the following examples. However, it should be understood that the following examples intend to illustrate the present invention, but do not limit the scope of the present invention in any way.

Preparation of the Compound

Example 1. Preparation of the Compound of Formula (III)

1. Solid Phase Synthesis of Peptide Chain 100 g of dichloro-tritylchloride resin (having a degree of substitution, of 1 mmol/g resin) was added into a 5 L reaction flask, to which 1 L dichloromethane was added. After 10 minutes, the resin sufficiently swelled in the solution, and 31.08 g of Fmoc-Tyr(tBu)—OH were added followed by 38 ml of DIEA. The reaction was continued for 30 minutes. Then, 1500 ml of methanol was added to terminate the reaction. The resin was filtered off, washed successively with isopropanol (IPA), DMF, isopropanol, DMF, isopropanol and ethyl ether, and dried in a fume hood to constant weight.

100 g of dried resin carrying Fmoc-Tyr(tBu)—OH was added into a 2 L reaction flask, and 1 L of DMF was added so that the resin sufficiently swelled in the solvent of DMF. DMF was drawn under a negative pressure into a waste liquid bottle, and 1 L of piperidine/DMF solution (25%) was added. The reaction flask was placed on a shaker at a speed of 120 rpm and the reaction was conducted for 30 minutes. Then, the deprotection solution was drawn under a negative pressure into a waste liquid bottle. The resin is washed successively with DMF, isopropanol, DMF, isopropanol and DMF, and all washings were transferred under a negative pressure to a waste liquid bottle.

66 g of Fmoc-Leu-OH, 30 ml of DIC, and 27 g of HOBt were added into a clean conical flask and were dissolved in 500 ml of DMF. After being activated on a shaker for 10 minutes, the activated solution was poured into the previous reaction flask. The reaction flask was placed on a shaker at a speed of 120 rpm for 120 minutes. After the reaction was completed, the reaction solution was drawn under a negative pressure into a waste liquid bottle. The resin was successively washed with DMF, isopropanol, DMF and isopropanol, and al washings were transferred under a negative pressure to a waste liquid bottle.

Following the above procedure, the protected amino acids of Fmoc-Gln(Trt)-OH, Fmoc-Val-OH, Fmoc-Ser(tBu)—OH, Fmoc-His(Trt)-OH and Fmoc-Val-OH were linked in sequence to the resin—Tyr(tBu)-Leu-OH, forming resin—Tyr(tBu)-Leu-Gln(Trt)-Val-Ser(tBu)-His(Trt)-Val-NH$_2$. The specific reaction reagents and the amounts used as well as the specific reaction parameters are shown in the following table (based on 100 g resin):

| Coupling sequence | Deprotection | Washing | Activation | Washing |
|---|---|---|---|---|
| 1 | piperidine/DMF (1:4), 30 min | DMF (1 L) IPA (1 L) 3 cycles | Fmoc-Gln(Trt)-OH 121 g, DIC 30 ml, HOBt 27 g | DMF (1 L) IPA (1 L) 3 cycles |
| 2 | piperidine/DMF (1:4), 30 min | DMF (1 L) IPA (1 L) 3 cycles | Fmoc-Val-OH 67.2 g, DIC 30 ml, HOBt 27 g | DMF (1 L) IPA (1 L) 3 cycles |
| 3 | piperidine/DMF (1:4), 30 min | DMF (1 L) IPA (1 L) 3 cycles | Fmoc-Ser(tBu)—OH 76 g, DIC 30 ml HOBt 27 g | DMF (1 L) IPA (1 L) 3 cycles |
| 4 | piperidine/DMF (1:4), 30 min | DMF (1 L) IPA (1 L) 3 cycles | Fmoc-His(Trt)-OH 122.8 g, DIC 30 ml HOBt 27 g | DMF (1 L) IPA (1 L) 3 cycles |
| 5 | piperidine/DMF (1:4), 30 min | DMF (1 L) IPA (1 L) 3 cycles | Fmoc-Val-OH 67.2 g, DIC 30 ml HOBt 27 g | DMF (1 L) IPA (1 L) 3 cycles |

2. Cleave of the Resin and Release of the Peptide Chain

The resin obtained after final washing was dried in a fume hood, and then was transferred to a 2 L round-bottom flask. After the addition of 1200 ml of TFA/H$_2$O (95:5), the round-bottom flask was placed on a shaker at 20 rpm to react for 2 hours. Then, the reaction solution was filtered through sand cores, and the filtrate was added in batches into 3 L of anhydrous ethyl ether. At this point, a large amount of white precipitates separated out. After standing for a while to full precipitation, filtering, through a Buchner funnel, washing with ethyl ether for three times, and weighting to give a crude product of the compound of formula (III).

3. Purification of the Crude Product

The resulting crude product of the compound of formula (III) was dissolved in purified water at a concentration of 25 mg/ml, and centrifuged. The undissolved part of the sample was discarded. Each 160 ml of the sample solution was loaded onto a HPLC dynamic axial compression column (ID 150 mm). Elution was carried out following gradient schemes for separation:

| Time (min) | Flow rate | Water (containing 0.1% of trifluoroacetic acid) | Acetonitrile (containing 0.1% of trifluoroacetic acid) |
| --- | --- | --- | --- |
| 0 | 430 | 14% | 86% |
| 10 | 430 | 14% | 86% |
| 70 | 430 | 26% | 74% |

Analytic HPLC was used to analyze the purity of each component. The samples having a purity of more than 98.5% were combined. The combined sample was evaporated on a rotary evaporator in a water bath of 40 Celsius degree and concentrated to a concentration of 10 mg/ml, and after being placed in a refrigerator to freeze, a pure product of the compound of formula (III) was obtained in a purity of more than 98%. LC-MS 845.42 [M+H]$^+$.

Biological Assessment

1. Materials
(1) Primary Reagents and Drugs

| Test compounds | self-made |
| --- | --- |
| Chloral hydrate | Sinopharm Chemical Reagent Co., Ltd |
| Red tetrazoline (TTC) | Sinopharm Chemical Reagent Co., Ltd |
| Paraformaldehyde | Shanghai Lingfeng Chemical Reagent Co., Ltd |

(2) Experimental Animals

Sprague-Dawley (SD) rats, male, weighing 280-320 g, clean, feeding, conditions: room temperature of 20-25° C., humidity of 30-60%, well ventilated, ad libitum diet; the animals were acclimatized in the feeding environment for three days prior to the experiment.

2. Establishment of the Right Cerebral Artery Ischemia/Reperfusion Model in Rats.

The rats were anesthetized with 4% chloral hydrate (350 mg/kg, ip.) and then were fixed in a supine position. A midline ventral neck incision was made, the right common carotid artery was separated and snared with two sutures for further use. Then, the internal carotid artery and external carotid artery were separated, and the external carotid artery was ligatured. The separated common carotid artery was ligatured at its proximal end with a thread, and the blood flow of the same was blocked at its distal end with a bulldog clamp. A small opening was cut therebetween and a nylon suture (4-0) which is heated at one end into a bead-like shape (having a diameter of <0.3 mm) was inserted into the small opening. The bulldog clamp was removed, and the nylon suture was gently advanced to the origin of the anterior cerebral artery (18-20 mm), thereby causing arterial ischemia in brain by blocking the blood supply of the cerebral artery. The skin was sutured and was sterilized with tincture of iodine. After 4 hours or 2 hours or 1.5 hours, the initial traumatic surface was open again by cutting and the nylon suture was withdrawn slowly from the common carotid artery which was ligatured with a suture and fixed. The skin was sutured again and was sterilized with tincture of iodine.

3. Assay of Cerebral Infarction Injury Rate in Rats

At different time after the operation, the animals were sacrificed and the brains were collected, from which the bulbus olfactories, opisthencephalon and low brain stem were removed. The brains were cut four times backward in a coronal plane using a die to divide it into five slices each having a thickness of 3 mm, wherein the first cut was made at the middle of the connecting line of brain anterior pole and optic chiasma, the second cut was made at the site of optic chiasma, the third cut was made at infundbular stalk, and the fourth cut was made between infundbular stalk and posterior pole of posterior pituitary. The slices were stained with 2% red tetrazolium (TTC): 1.5 ml of 2% TTC, 3.4 ml of saline, and incubated in dark at 37° C. for 30 min. Normal tissues appeared in red, while infarct tissues appeared in white or showed stroke capsules which are defected when slicing. The five brain slices were arranged in original order and photographed. The percentage of cerebral infarction injury was calculated as a volume (area) percentage of the remaining volume (area) in the infarct cerebral hemisphere to the volume (area) of the contralateral cerebral hemisphere.

4. Preparation of Test Samples

The compound of formula (III) was dissolved in PBS subjected to high temperature sterilization at 121° C. to formulate various solutions of 0.1-9.6 mg/ml, which was filtered through a millipore filter membrane of 22 μm and stored in a refrigerator at 4° C. until use. The entire preparation process was carried out in a super clean bench.

5. Administration Method

From the beginning of the administration, various doses of 0.1-9.6 mg/kg were injected intraperitoneally into respective animal groups once a day.

6. Neurological Score

Neurologic deficit scores were assessed for the above experimental animals according to the following procedure before the beginning of experiment and 24 hours, 1 day, 3 days, 7 days, 14 days, 28 days, 56 days, and 112 days after the beginning of experiment; Score rules: see Zea Longer score and NSS score, full score of 10;

(i) Lifting an animal by tail: (full score of 1)

| Fore limbs flexing | 1 |
| --- | --- |

(ii) Observation of animals placed on the ground: (full score of 4)

| Walking normally with physical agility | 0 |
| --- | --- |
| Acting slowly, being unable to walk straight, and failing to stretch contralateral limbs fully | 1 |
| Circling toward the contralateral side | 2 |
| Falling toward the contralateral side or falling down when walking | 3 |
| Being unable to walk spontaneously accompanied by severe loss of consciousness | 4 |

(iii) Observations of animals placed on a balance beam: (full score of 4)

| | |
|---|---|
| Walking evenly, stably, and promptly | 0 |
| The animals could walk, but one limb slid down or turned around on the balance beam for a long time | 1 |
| The animals could not walk smoothly, two hind legs slid down, but they could stay on the balance beam stably without falling | 2 |
| The animals tried to grab the balance beam, but still fell | 3 |
| The animals did not try to grab the balance beam, and directly fell | 4 |

(iv) observing the animal's condition: (full score of 1)

| | |
|---|---|
| Horner syndrome appeared, the head skews toward one side, one eye lid drooped and there was no obvious bleeding around the eyes | 1 |

Example 2

Normal male SD rats, weighing 280~320 g, were used in six experiments on 1.5-hour ischemia/reperfusion model groups (I1.5R+ model). Monitoring the scores of neuroethology symptoms 24 hours after the cerebral ischemia reperfusion injury and at each subsequent week in rats of the 1.5-hours ischemia/reperfusion model groups. The final results and sample size: results from the I1.5R+ model group in six experiments were combined (animal data: 31 animals in total in the I1.5R+model groups. In addition, the data of first week was the combined data from the experimental groups and the model group, the animal number in the 24-hour data was 101, and the animal number in the first week, data was 106).

Figure 2:
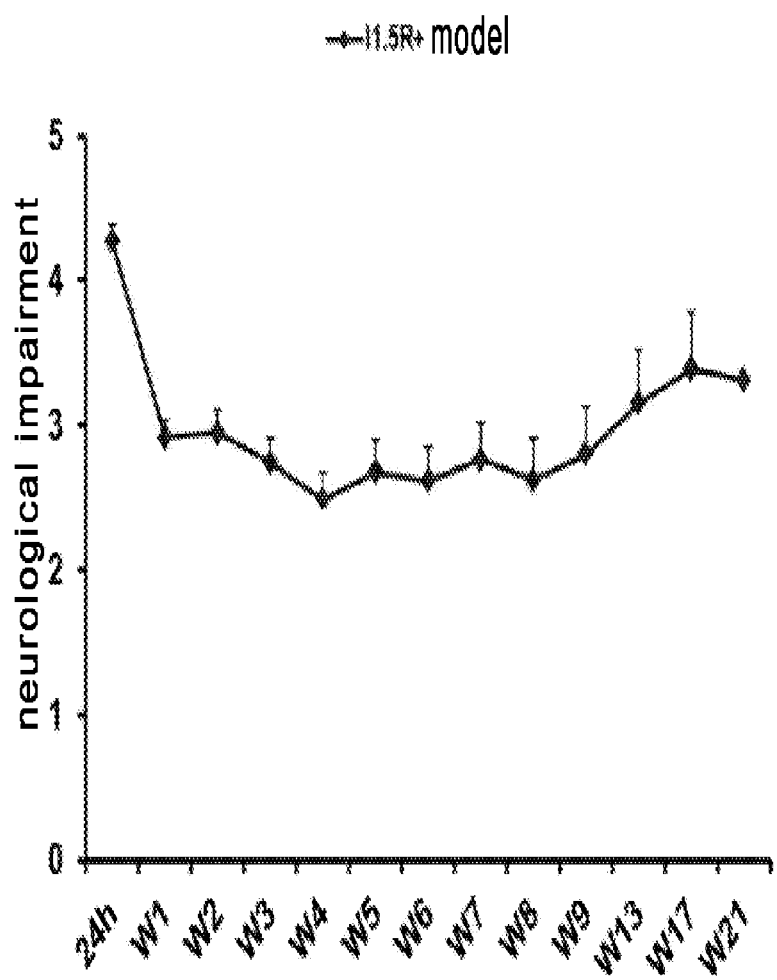
FIG. 2 illustrates the neurologic deficit scores of rats at different times (observed until 22 weeks) in a rat 1.5 h ischemia-reperfusion model.

The weights and scores of SD rats in the 1.5-hour ischemia/reperfusion model were recorded at 1.0 different time points later. The results showed that the weights of SD rats in the 1.5-hour ischemia/reperfusion showed a tendency of gradually rising, and the neurological score of 24-hour was slightly greater than 4 and decreased down to 3 at one week, then the score fluctuated around 3 for a long time. The detailed results were shown in FIGS. 1 and 2. The assay of cerebral infarction injury ratio in rats was seen in FIGS. 7 and 8A-8C.

Example 3

Normal male SD rats, weighing 280~320 g, were used in three experiments. In the first experiment, animals were divided randomly into two groups, one group in which the administration started one week after the 1.5-hour ischemia/reperfusion and continued for four weeks (I1.5R+1 week+dosing for 4 weeks), and the other group for the 1.5-hour ischemia/reperfusion model without administering, the compound of formula (III) (I1.5R+model). In the second experiment, animals were divided randomly into two groups, one group in which the administration started two weeks after the 1.5-hour ischemia/reperfusion and continued for four weeks (I1.5R+2 weeks+dosing for 4 weeks), and the other group for the 1.5-hour ischemia/reperfusion model without administering, the compound of formula (III) (I1.5R+model).

In the third experiment, animals were divided randomly into two groups, one group in which the administration started three days after the 1.5-hour ischemia/reperfusion and continued for four weeks (I1.5R+3 days+dosing for 4 weeks) and the other group for the 1.5-hour ischemia/reperfusion model without administering the compound of formula (III) (I1.5R+model). The three treatment groups with different start times of administration were all dosed at a dose of 3.6 mg/kg by intraperitoneal injection once a day from the beginning of administration for four weeks. Monitoring the scores of neuroethology symptoms 24 hours after the cerebral ischemia reperfusion injury and at each subsequent week (including each week during and after the administration) in rats of each group. The final results and sample size: the combined chart of five experimental results from the I1.5R+1 week+dosing 4 weeks group (animal data: I1.5R+1 week group, 31 animals in total); the chart of experimental result from the I1.5R+2 week+dosing for 4 weeks group (animal data: I1.5R+2 weeks+dosing for 4 weeks group, 9 animals in total).

Figure 3:
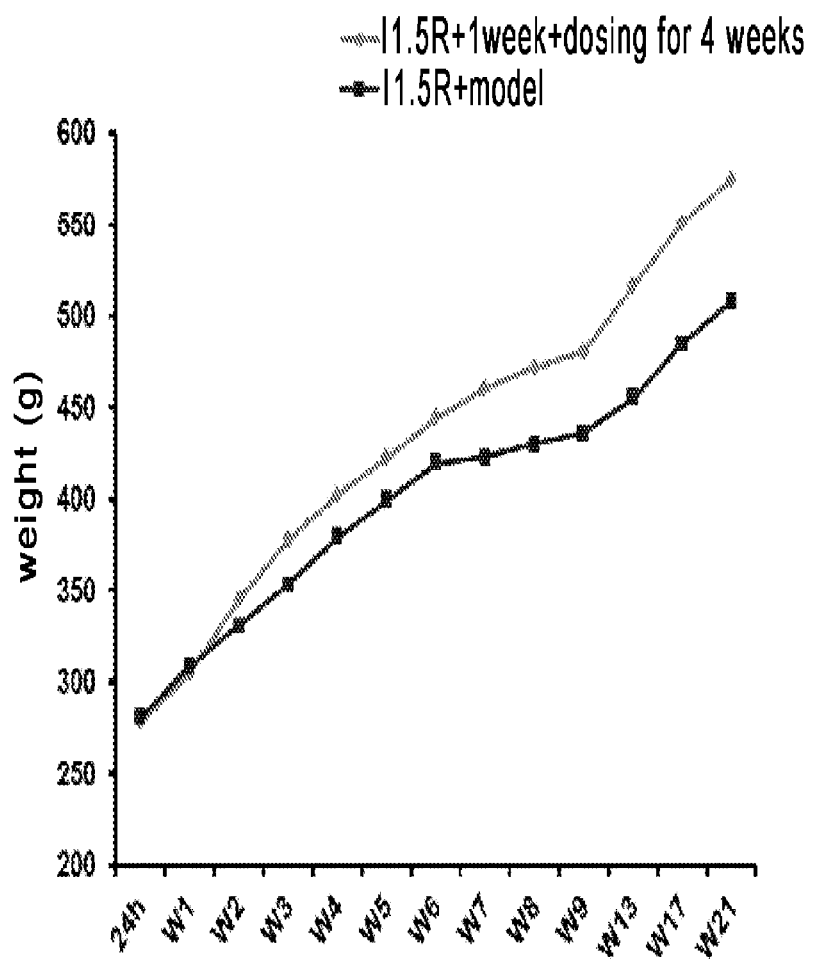
FIG. 3 illustrates the therapeutic effects of compound of formula (III) on rats continuously administered for 4 weeks after 1.5 h ischemia and one week reperfusion (observed until 22 weeks)—weight condition.
Figure 4:
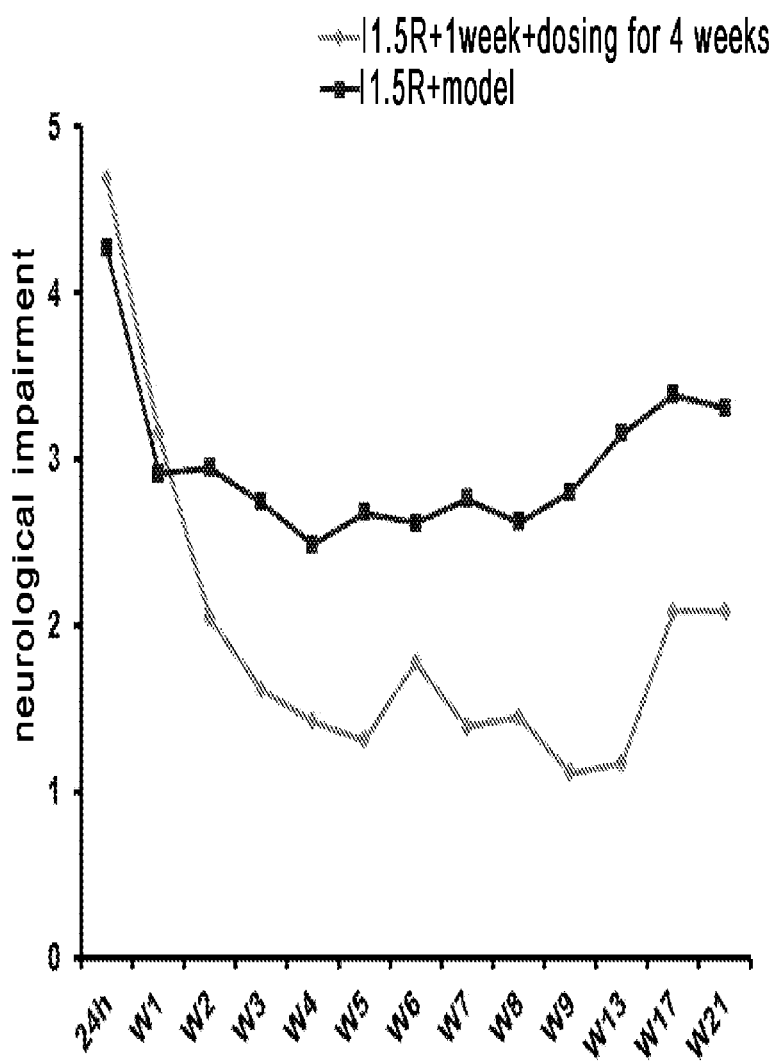
FIG. 4 illustrates the therapeutic effects of compound of formula (III) on rats continuously administered for 4 weeks after 1.5 h ischemia and one week reperfusion (observed until 22 weeks)—neurologic deficit score.

The weight and score change after administration of the compound of formula (III) one week after the 1.5-hour ischemia/reperfusion for four weeks. The results showed that, compared to the model group without administering, the compound of formula (III), the animals in the I1.5R+ week+dosing for 4 weeks group had a gradually increased weight from the beginning of the administration and a gradually declined neuroethology score, and the data results of neuroethology score are statistically significant in the second, third, fourth, fifth and seventh week after the operation. The detailed results are shown in FIGS. 3 and 4.

Figure 5:
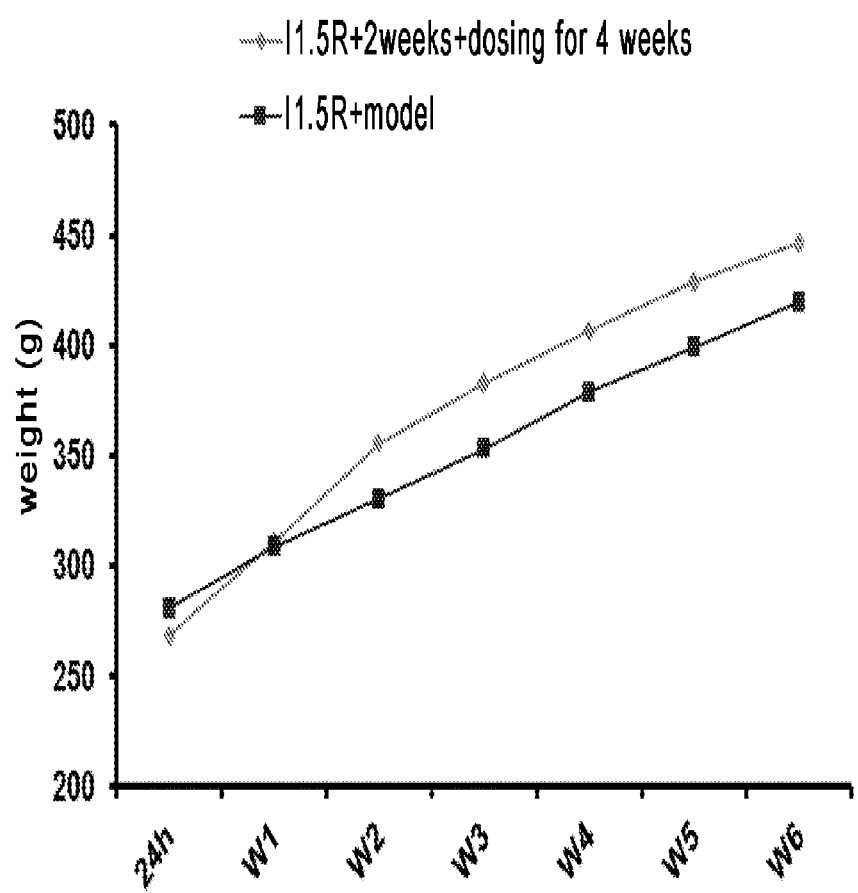
FIG. 5 illustrates the therapeutic effects of compound of formula (III) on rats continuously administered for 4 weeks after 1.5 h ischemia and two week reperfusion (observed until 7 weeks)—weight condition.
Figure 6:
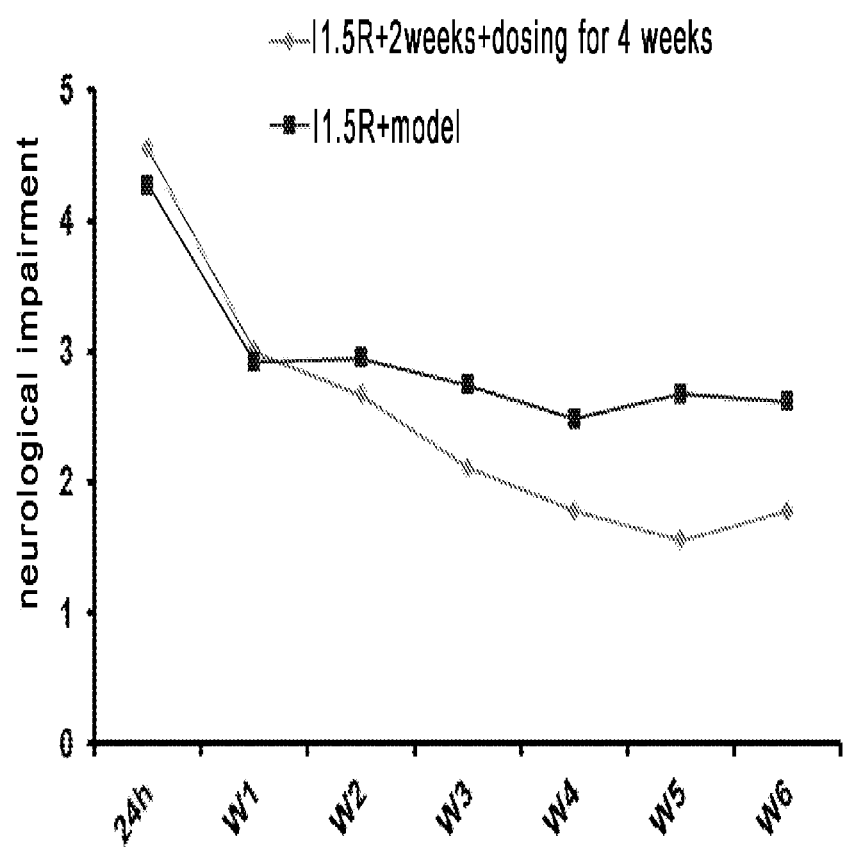
FIG. 6 illustrates the therapeutic effects of compound of formula (III) on rats continuously administered for 4 weeks after 1.5 h ischemia and two week reperfusion (observed until 7 weeks)—neurologic deficit score.
Figure 7:
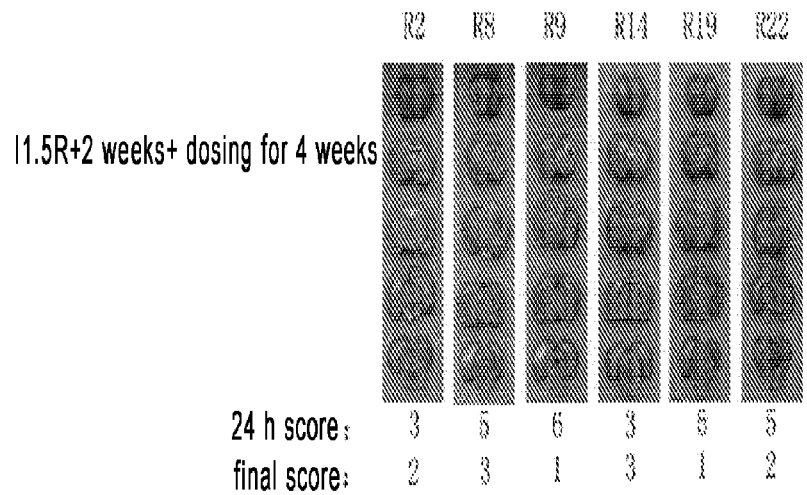
FIG. 7 illustrates the measurement results of cerebral infarction injury rate in rats (treated with continuous administration for 4 weeks after 1.5 h ischemia and two week reperfusion).
Figure 7:
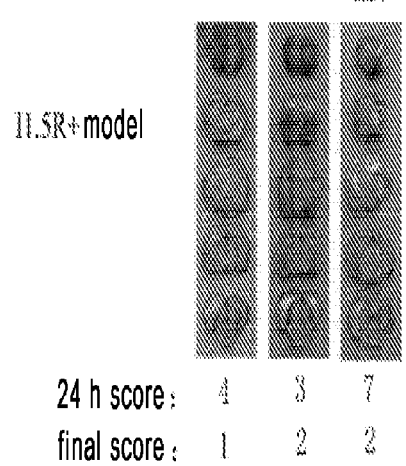
Figure 8A:
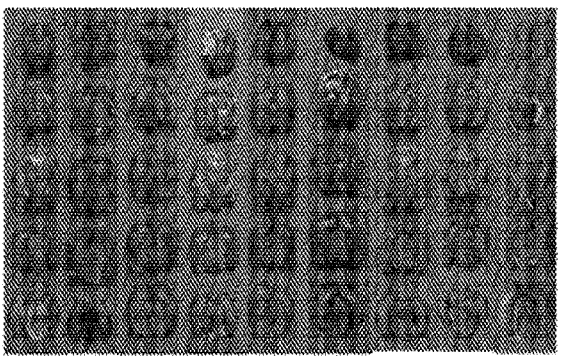
FIGS. 8A-8C illustrate the measurement results of cerebral infarction injury rate in rats treated with continuous administration for 4 weeks after 1.5 h ischemia and one week reperfusion (FIG. 8A) or 3 days reperfusion (FIG. 8C), after 1.5 h ischemia (FIG. 8B).
Figure 8:
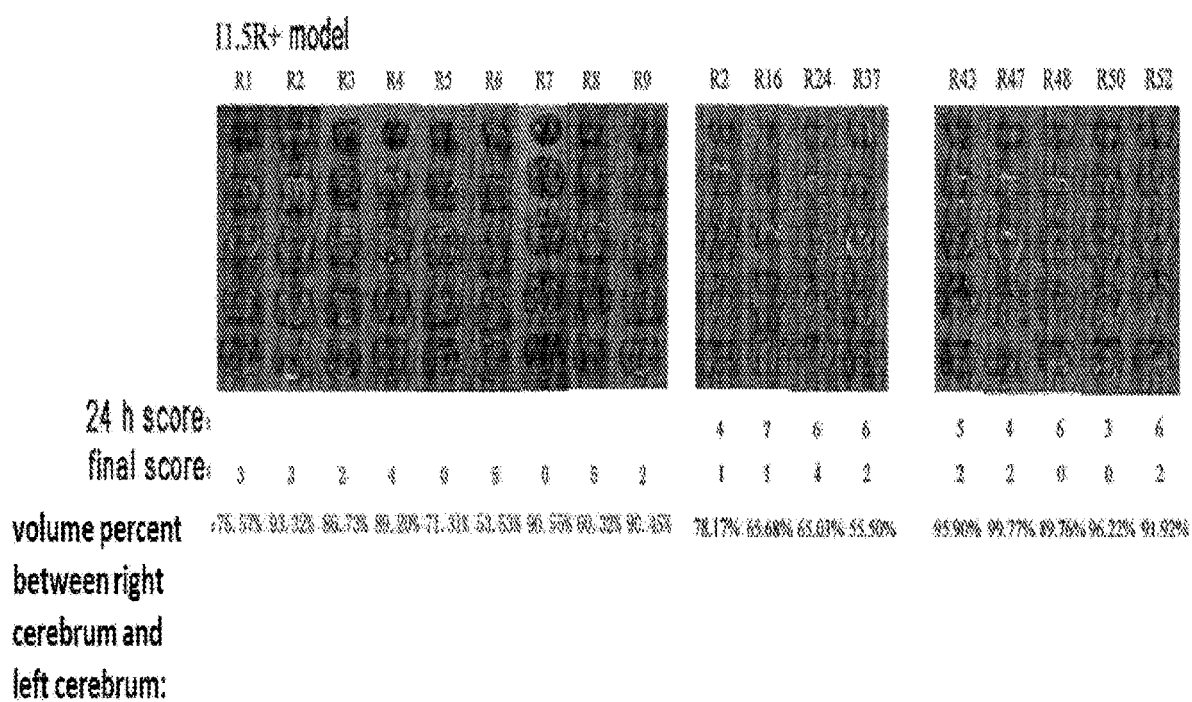
Figure 8:
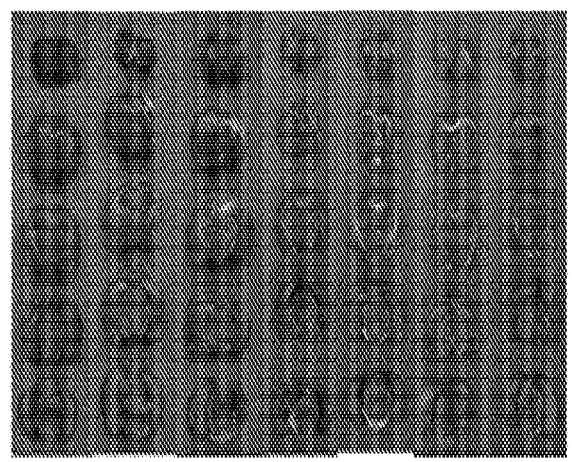

The weight and score change after administration of the compound of formula (III) two weeks after the 1.5-hour ischemia/reperfusion for four weeks. The results showed that, compared to the model group without administering the compound of formula (III), the animals in the I1.5R+2 weeks+dosing for 4 weeks group had a gradually increased weight from the beginning of administration, however the weight data of the administration group cannot be demonstrative, since the data of the administration group had been statistically significant over the model group without administering the compound of formula (III) before the beginning of the administration. In the meantime, the neurological scores of the I1.5R+2 weeks+dosing for 4 weeks group declined from the beginning of the administration compared to the model group without administering the compound of formula (III), and the score data are statistically significant at the fifth week after the operation. The results are shown in FIGS. 5 and 6. The measurement results of cerebral infarction injury ratio in rats are shown in FIGS. 7 and 8A-8C.

Based on the above experimental data, it can be seen that the pharmaceutical composition comprising the compound according to the present invention has evident effects for the treatment or improvement of sequelae of ischemic cerebral stroke. Without departing from the concept of the present invention, suitable modifications or variations based on the present invention fall within the scope of the present invention.

The invention claimed is:

1. A method of treating sequelae of ischemic cerebral stroke, comprising administering a therapeutically effective amount of a synthesized compound or a pharmaceutically acceptable salt thereof, to a subject, wherein the compound is:

(SEQ ID NO.: 1)

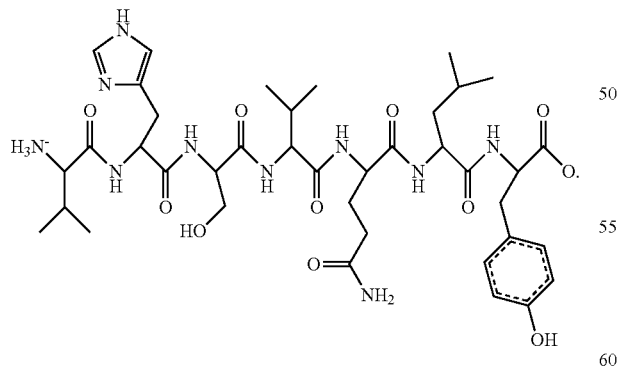

2. The method of claim 1, wherein the pharmaceutically acceptable salt is selected from the group consisting of an organic acid salt, an inorganic acid salt, an alkali metal salt, an alkali earth metal salt, and an inner salt of the compound.

* * * * *